US005965699A

United States Patent [19]

Schmidt et al.

[11] Patent Number: 5,965,699
[45] Date of Patent: Oct. 12, 1999

[54] ASSAY FOR THE PROTEOLYTIC ACTIVITY OF SEROTYPE A FROM CLOSTRIDIUM BOTULINUM

[75] Inventors: James J. Schmidt, Mt. Airy; Karen A. Bostian, Frederick, both of Md.

[73] Assignee: The United States of America as represented by the Secretary of the Army, Washington, D.C.

[21] Appl. No.: 08/743,894

[22] Filed: Nov. 6, 1996

[51] Int. Cl.$^6$ ............... C07K 7/00; C12Q 1/00; G01N 33/52
[52] U.S. Cl. ............ 530/326; 530/300; 530/350; 530/324; 530/325; 530/327; 530/328; 530/329; 530/330; 530/333; 530/335; 530/337; 530/839; 435/4; 435/7.72; 435/252.7; 435/842; 435/7.71; 435/7.1; 435/183; 930/10; 930/20; 514/2
[58] Field of Search ............ 435/4, 7.72, 252.7, 435/842, 7.71, 7.1, 183; 530/333, 337, 335, 300, 350, 324–330, 839; 514/2; 930/10, 20

[56] References Cited

U.S. PATENT DOCUMENTS 4,701,328 10/1987 Bercovici et al. .

FOREIGN PATENT DOCUMENTS 9533850 3/1994 WIPO .

OTHER PUBLICATIONS

Hallus et al. (Aug. 1996) J–Clin, Microbiol. vol. 34(8) 1934–1938.
Galen et al. Biochemica et Biophipica Acta 523:485–93, 1978.

Primary Examiner—Anthony C. Caputa
Assistant Examiner—Khalid Masood
Attorney, Agent, or Firm—Charles H. Harris; John Francis Moran

[57] ABSTRACT

A label-based assay is described, through modifications of substrate structure and derivatization of serum albumin, which can be used to determine type A proteolytic activity without separation of products.

13 Claims, 1 Drawing Sheet

SEQUENCE LISTING (1) GENERAL INFORMATION:

(iii) NUMBER OF SEQUENCES: 56

(2) INFORMATION FOR SEQ ID NO:1:

(i) SEQUENCE CHARACTERISTICS:
      (A) LENGTH: 17 amino acids
      (B) TYPE: amino acid sequence
      (C) STRANDEDNESS: Single
      (D) TOPOLOGY: Linear (ii) SEQUENCE DESCRIPTION: SEQ ID NO:1:

Ser Asn Lys Thr Arg Ile Asp Glu Ala Asn
1               5                    10

Gln Arg Ala Thr Lys Met Leu
            15

(2) INFORMATION FOR SEQ ID NO:2:

(i) SEQUENCE CHARACTERISTICS:
      (A) LENGTH: 17 amino acids
      (B) TYPE: amino acid sequence
      (C) STRANDEDNESS: Single
      (D) TOPOLOGY: Linear (ii) SEQUENCE DESCRIPTION: SEQ ID NO:2:

```
Ser Asn Arg Thr Arg Ile Asp Glu Ala Asn
1               5                   10

Gln Arg Ala Thr Arg Met Leu
                15
```

(2) INFORMATION FOR SEQ ID NO:3:

(i) SEQUENCE CHARACTERISTICS:
        (A) LENGTH: 17 amino acids
        (B) TYPE: amino acid sequence
        (C) STRANDEDNESS: Single
        (D) TOPOLOGY: Linear (ii) SEQUENCE DESCRIPTION: SEQ ID NO:3:

```
Ser Asn Arg Thr Arg Ile Asp Gln Ala Asn
1               5                   10

Gln Arg Ala Thr Arg Met Leu
                15
```

(2) INFORMATION FOR SEQ ID NO:4:

(i) SEQUENCE CHARACTERISTICS:
        (A) LENGTH: 17 amino acids
        (B) TYPE: amino acid sequence
        (C) STRANDEDNESS: Single
        (D) TOPOLOGY: Linear (ix) FEATURE:
        (B) LOCATION: 4
        (D) OTHER INFORMATION: Xaa represent Abu, or 2-Aminobutyric
            Acid (ii) SEQUENCE DESCRIPTION: SEQ ID NO:4:

```
Ser Asn Arg Xaa Arg Ile Asp Glu Ala Asn
1               5                   10

Gln Arg Ala Thr Arg Met Leu
                15
```

(2) INFORMATION FOR SEQ ID NO:5:

(i) SEQUENCE CHARACTERISTICS:
        (A) LENGTH: 17 amino acids
        (B) TYPE: amino acid sequence
        (C) STRANDEDNESS: Single
        (D) TOPOLOGY: Linear (ix) FEATURE:
        (B) LOCATION: 14
        (D) OTHER INFORMATION: Xaa represent Abu, or 2-Aminobutyric
            Acid (ii) SEQUENCE DESCRIPTION: SEQ ID NO:5:

```
Ser Asn Arg Thr Arg Ile Asp Glu Ala Asn
1               5                   10

Gln Arg Ala Xaa Arg Met Leu
                15
```

(2) INFORMATION FOR SEQ ID NO:6:

(i) SEQUENCE CHARACTERISTICS:
        (A) LENGTH: 17 amino acids
        (B) TYPE: amino acid sequence
        (C) STRANDEDNESS: Single
        (D) TOPOLOGY: Linear (ix) FEATURE:
        (B) LOCATION: 16
        (D) OTHER INFORMATION: Xaa represent Nle, or Noreleucine (ii) SEQUENCE DESCRIPTION: SEQ ID NO:6:

Ser Asn Arg Thr Arg Ile Asp Glu Ala Asn
1               5                   10

Gln Arg Ala Thr Arg Xaa Leu
                15

(2) INFORMATION FOR SEQ ID NO:7:

(i) SEQUENCE CHARACTERISTICS:
        (A) LENGTH: 16 amino acids
        (B) TYPE: amino acid sequence
        (C) STRANDEDNESS: Single
        (D) TOPOLOGY: Linear (ix) FEATURE:
        (B) LOCATION: 4
        (D) OTHER INFORMATION: Xaa represent Abu, or 2-Aminobutyric
            Acid (ii) SEQUENCE DESCRIPTION: SEQ ID NO:7:

Ser Asn Arg Xaa Arg Ile Asp Glu Ala Asn
1               5                   10

Gln Arg Ala Thr Arg Met
                15

(2) INFORMATION FOR SEQ ID NO:8:

(i) SEQUENCE CHARACTERISTICS:
        (A) LENGTH: 17 amino acids
        (B) TYPE: amino acid sequence
        (C) STRANDEDNESS: Single
        (D) TOPOLOGY: Linear (ix) FEATURE:
        (B) LOCATION: 4
        (D) OTHER INFORMATION: Xaa represent Abu, or 2-Aminobutyric
            Acid (ii) SEQUENCE DESCRIPTION: SEQ ID NO:8:

Ser Asn Arg Xaa Arg Ile Asp Gln Ala Asn
1               5                   10

Gln Arg Ala Thr Arg Met Leu
                15

(2) INFORMATION FOR SEQ ID NO:9:

(i) SEQUENCE CHARACTERISTICS:
        (A) LENGTH: 16 amino acids
        (B) TYPE: amino acid sequence
        (C) STRANDEDNESS: Single
        (D) TOPOLOGY: Linear (ix) FEATURE:
        (B) LOCATION: 4
        (D) OTHER INFORMATION: Xaa represent Abu, or 2-Aminobutyric
            Acid (ii) SEQUENCE DESCRIPTION: SEQ ID NO:9:

Ser Asn Arg Xaa Arg Ile Asp Gln Ala Asn
1               5                   10

Gln Arg Ala Thr Arg Met
                15

(2) INFORMATION FOR SEQ ID NO:10:

(i) SEQUENCE CHARACTERISTICS:
        (A) LENGTH: 17 amino acids
        (B) TYPE: amino acid sequence

```
            (C) STRANDEDNESS: Single
            (D) TOPOLOGY: Linear (ix) FEATURE:
            (B) LOCATION: 4 and 8
            (D) OTHER INFORMATION: Xaa represent Abu, or 2-Aminobutyric
                Acid (ii) SEQUENCE DESCRIPTION: SEQ ID NO:10:

Ser Asn Arg Xaa Arg Ile Asp Xaa Ala Asn
1               5                   10

Gln Arg Ala Thr Arg Met Leu
                15

(2) INFORMATION FOR SEQ ID NO:11:

(i) SEQUENCE CHARACTERISTICS:
            (A) LENGTH: 16 amino acids
            (B) TYPE: amino acid sequence
            (C) STRANDEDNESS: Single
            (D) TOPOLOGY: Linear (ix) FEATURE:
            (B) LOCATION: 4 and 8
            (D) OTHER INFORMATION: Xaa represent Abu, or 2-Aminobutyric
                Acid (ii) SEQUENCE DESCRIPTION: SEQ ID NO:11:

Ser Asn Arg Xaa Arg Ile Asp Xaa Ala Asn
1               5                   10

Gln Arg Ala Thr Arg Met
                15

(2) INFORMATION FOR SEQ ID NO:12:

(i) SEQUENCE CHARACTERISTICS:
            (A) LENGTH: 16 amino acids
            (B) TYPE: amino acid sequence
            (C) STRANDEDNESS: Single
            (D) TOPOLOGY: Linear (ix) FEATURE:

(ii) SEQUENCE DESCRIPTION: SEQ ID NO:12:

Ser Asn Arg Thr Arg Ile Asp Gln Ala Asn
1               5                   10

Gln Arg Ala Thr Arg Met
                15

(2) INFORMATION FOR SEQ ID NO:13:

(i) SEQUENCE CHARACTERISTICS:
            (A) LENGTH: 16 amino acids
            (B) TYPE: amino acid sequence
            (C) STRANDEDNESS: Single
            (D) TOPOLOGY: Linear (ix) FEATURE:
            (B) LOCATION: 8
            (D) OTHER INFORMATION: Xaa represent Abu, or 2-Aminobutyric
                Acid (ii) SEQUENCE DESCRIPTION: SEQ ID NO:13:

Ser Asn Arg Thr Arg Ile Asp Xaa Ala Asn
1               5                   10

Gln Arg Ala Thr Arg Met
                15
```

(2) INFORMATION FOR SEQ ID NO:14:

(i) SEQUENCE CHARACTERISTICS:
        (A) LENGTH: 17 amino acids
        (B) TYPE: amino acid sequence
        (C) STRANDEDNESS: Single
        (D) TOPOLOGY: Linear (ix) FEATURE:
        (B) LOCATION: 8
        (D) OTHER INFORMATION:Xaa represent Abu, or 2-Aminobutyric
            Acid (ii) SEQUENCE DESCRIPTION: SEQ ID NO:14:

```
Ser Asn Arg Thr Arg Ile Asp Xaa Ala Asn
1               5                   10

Gln Arg Ala Thr Arg Met Leu
                15
```

(2) INFORMATION FOR SEQ ID NO:15:

(i) SEQUENCE CHARACTERISTICS:
        (A) LENGTH: 17 amino acids
        (B) TYPE: amino acid sequence
        (C) STRANDEDNESS: Single
        (D) TOPOLOGY: Linear (ix) FEATURE:
        (B) LOCATION: 4 and 14
        (D) OTHER INFORMATION: Xaa represents Abu, or 2-Aminobutyric
            Acid (ix) FEATURE:
        (B) LOCATION: 16
        (D) OTHER INFORMATION:Xaa represents Norleucine (ii) SEQUENCE DESCRIPTION: SEQ ID NO:15:

```
Ser Asn Arg Xaa Arg Ile Asp Gln Ala Asn
1               5                   10

Gln Arg Ala Xaa Arg Xaa Leu
                15
```

(2) INFORMATION FOR SEQ ID NO:16:

(i) SEQUENCE CHARACTERISTICS:
        (A) LENGTH: 13 amino acids
        (B) TYPE: amino acid sequence
        (C) STRANDEDNESS: Single
        (D) TOPOLOGY: Linear (ix) FEATURE:

(ii) SEQUENCE DESCRIPTION: SEQ ID NO:16:

```
Thr Arg Ile Asp Glu Ala Asn Gln Arg Ala
1               5                   10

Thr Arg Met
        13
```

(2) INFORMATION FOR SEQ ID NO:17:

(i) SEQUENCE CHARACTERISTICS:
        (A) LENGTH: 12 amino acids
        (B) TYPE: amino acid sequence
        (C) STRANDEDNESS: Single
        (D) TOPOLOGY: Linear (ix) FEATURE:

(ii) SEQUENCE DESCRIPTION: SEQ ID NO:17:

Arg Ile Asp Glu Ala Asn Gln Arg Ala Thr

```
1               5              10
Arg Met
    12

(2) INFORMATION FOR SEQ ID NO:18:

(i) SEQUENCE CHARACTERISTICS:
        (A) LENGTH: 17 amino acids
        (B) TYPE: amino acid sequence
        (C) STRANDEDNESS: Single
        (D) TOPOLOGY: Linear (ix) FEATURE:

(ii) SEQUENCE DESCRIPTION: SEQ ID NO:18:

Ser Asn Lys Thr Arg Ile Asp Gln Ala Asn
1               5              10

Gln Arg Ala Thr Lys Met Leu
            15

(2) INFORMATION FOR SEQ ID NO:19:

(i) SEQUENCE CHARACTERISTICS:
        (A) LENGTH: 17 amino acids
        (B) TYPE: amino acid sequence
        (C) STRANDEDNESS: Single
        (D) TOPOLOGY: Linear (ix) FEATURE:
        (B) LOCATION: 4
        (D) OTHER INFORMATION: Xaa represents Abu, or 2-Aminobutyric
            Acid (ii) SEQUENCE DESCRIPTION: SEQ ID NO:19:

Ser Asn Lys Xaa Arg Ile Asp Glu Ala Asn
1               5              10

Gln Arg Ala Thr Lys Met Leu
            15

(2) INFORMATION FOR SEQ ID NO: 20:

(i) SEQUENCE CHARACTERISTICS:
        (A) LENGTH: 17 amino acids
        (B) TYPE: amino acid sequence
        (C) STRANDEDNESS: Single
        (D) TOPOLOGY: Linear (ix) FEATURE:
        (B) LOCATION: 8
        (D) OTHER INFORMATION: Xaa represents Abu, or 2-Aminobutyric
            Acid (ii) SEQUENCE DESCRIPTION: SEQ ID NO:20:

Ser Asn Lys Thr Arg Ile Asp Xaa Ala Asn
1               5              10

Gln Arg Ala Thr Lys Met Leu
            15

(2) INFORMATION FOR SEQ ID NO: 21:

(i) SEQUENCE CHARACTERISTICS:
        (A) LENGTH: 17 amino acids
        (B) TYPE: amino acid sequence
        (C) STRANDEDNESS: Single
        (D) TOPOLOGY: Linear (ix) FEATURE:
        (B) LOCATION: 4
        (D) OTHER INFORMATION: Xaa represents Abu, or 2-Aminobutyric
```

Acid (ii) SEQUENCE DESCRIPTION: SEQ ID NO:21:

Ser Asn Lys Xaa Arg Ile Asp Gln Ala Asn
1               5                   10

Gln Arg Ala Thr Lys Met Leu
                15

(2) INFORMATION FOR SEQ ID NO: 22:

(i) SEQUENCE CHARACTERISTICS:
        (A) LENGTH: 17 amino acids
        (B) TYPE: amino acid sequence
        (C) STRANDEDNESS: Single
        (D) TOPOLOGY: Linear (ix) FEATURE:
        (B) LOCATION: 4 and 8
        (D) OTHER INFORMATION: Xaa represents Abu, or 2-Aminobutyric
            Acid (ii) SEQUENCE DESCRIPTION: SEQ ID NO:22:

Ser Asn Lys Xaa Arg Ile Asp Xaa Ala Asn
1               5                   10

Gln Arg Ala Thr Lys Met Leu
                15

(2) INFORMATION FOR SEQ ID NO: 23:

(i) SEQUENCE CHARACTERISTICS:
        (A) LENGTH: 17 amino acids
        (B) TYPE: amino acid sequence
        (C) STRANDEDNESS: Single
        (D) TOPOLOGY: Linear (ix) FEATURE:

(ii) SEQUENCE DESCRIPTION: SEQ ID NO:23:

Ser Asn Arg Ser Arg Ile Asp Glu Ala Asn
1               5                   10

Gln Arg Ala Thr Arg Met Leu
                15

(2) INFORMATION FOR SEQ ID NO: 24:

(i) SEQUENCE CHARACTERISTICS:
        (A) LENGTH: 17 amino acids
        (B) TYPE: amino acid sequence
        (C) STRANDEDNESS: Single
        (D) TOPOLOGY: Linear (ix) FEATURE:
        (B) LOCATION: 16
        (D) OTHER INFORMATION: Xaa represents norleucine (ii) SEQUENCE DESCRIPTION: SEQ ID NO:24:

Ser Asn Lys Thr Arg Ile Asp Glu Ala Asn
1               5                   10

Gln Arg Ala Thr Lys Xaa Leu
                15

(2) INFORMATION FOR SEQ ID NO: 25:

(i) SEQUENCE CHARACTERISTICS:
        (A) LENGTH: 17 amino acids
        (B) TYPE: amino acid sequence
        (C) STRANDEDNESS: Single
        (D) TOPOLOGY: Linear (ix) FEATURE:
              (B) LOCATION: 14
              (D) OTHER INFORMATION: Xaa represents Abu, or 2-Aminobutyric
                  Acid (ii) SEQUENCE DESCRIPTION: SEQ ID NO:25:

Ser Asn Lys Thr Arg Ile Asp Glu Ala Asn
1               5                   10

Gln Arg Ala Xaa Lys Met Leu
            15

(2) INFORMATION FOR SEQ ID NO: 26:

(i) SEQUENCE CHARACTERISTICS:
              (A) LENGTH: 17 amino acids
              (B) TYPE: amino acid sequence
              (C) STRANDEDNESS: Single
              (D) TOPOLOGY: Linear (ix) FEATURE:

(ii) SEQUENCE DESCRIPTION: SEQ ID NO:26:

Ser Asn Lys Thr Arg Ile Asp Glu Ala Asn
1               5                   10

Gln Arg Ala Cys Lys Met Leu
            15

(2) INFORMATION FOR SEQ ID NO: 27:

(i) SEQUENCE CHARACTERISTICS:
              (A) LENGTH: 17 amino acids
              (B) TYPE: amino acid sequence
              (C) STRANDEDNESS: Single
              (D) TOPOLOGY: Linear (ix) FEATURE:
              (B) LOCATION: 13
              (D) OTHER INFORMATION: Xaa represent Abu, or 2-Aminobutyric
                  Acid (ii) SEQUENCE DESCRIPTION: SEQ ID NO:27:

Ser Asn Lys Thr Arg Ile Asp Glu Ala Asn
1               5                   10

Gln Arg Xaa Thr Lys Met Leu
            15

(2) INFORMATION FOR SEQ ID NO: 28:

(i) SEQUENCE CHARACTERISTICS:
              (A) LENGTH: 17 amino acids
              (B) TYPE: amino acid sequence
              (C) STRANDEDNESS: Single
              (D) TOPOLOGY: Linear (ix) FEATURE:

(ii) SEQUENCE DESCRIPTION: SEQ ID NO:28:

Ser Asn Lys Thr Arg Ile Asp Glu Ala Asn
1               5                   10

Gln Arg Ala Thr Lys Ala Leu
            15

(2) INFORMATION FOR SEQ ID NO: 29:

(i) SEQUENCE CHARACTERISTICS:
              (A) LENGTH: 17 amino acids
              (B) TYPE: amino acid sequence (C) STRANDEDNESS: Single
        (D) TOPOLOGY: Linear (ix) FEATURE:

(ii) SEQUENCE DESCRIPTION: SEQ ID NO:29:

Ser Asn Lys Thr Arg Ile Asp Glu Ala Asn
1               5                   10

Asn Arg Ala Thr Lys Met Leu
                15

(2) INFORMATION FOR SEQ ID NO: 30:

(i) SEQUENCE CHARACTERISTICS:
        (A) LENGTH: 17 amino acids
        (B) TYPE: amino acid sequence
        (C) STRANDEDNESS: Single
        (D) TOPOLOGY: Linear (ix) FEATURE:
        (B) LOCATION: 9
        (D) OTHER INFORMATION: Xaa represents Abu, or 2-Aminobutyric
            Acid (ii) SEQUENCE DESCRIPTION: SEQ ID NO:30:

Ser Asn Lys Thr Arg Ile Asp Glu Xaa Asn
1               5                   10

Gln Arg Ala Thr Lys Met Leu
                15

(2) INFORMATION FOR SEQ ID NO: 31:

(i) SEQUENCE CHARACTERISTICS:
        (A) LENGTH: 17 amino acids
        (B) TYPE: amino acid sequence
        (C) STRANDEDNESS: Single
        (D) TOPOLOGY: Linear (ix) FEATURE:

(ii) SEQUENCE DESCRIPTION: SEQ ID NO:31:

Ser Asn Lys Thr Arg Ile Asp Glu Ala Asn
1               5                   10

Gln Arg Ala Thr Ala Met Leu
                15

(2) INFORMATION FOR SEQ ID NO: 32:

(i) SEQUENCE CHARACTERISTICS:
        (A) LENGTH: 17 amino acids
        (B) TYPE: amino acid sequence
        (C) STRANDEDNESS: Single
        (D) TOPOLOGY: Linear (ix) FEATURE:

(ii) SEQUENCE DESCRIPTION: SEQ ID NO:32:

Ser Asn Lys Thr Arg Ile Asp Glu Ala Asn
1               5                   10

Gln Arg Ala Ser Lys Met Leu
                15

(2) INFORMATION FOR SEQ ID NO: 33:

(i) SEQUENCE CHARACTERISTICS:
        (A) LENGTH: 17 amino acids
        (B) TYPE: amino acid sequence
        (C) STRANDEDNESS: Single (D) TOPOLOGY: Linear (ix) FEATURE:

(ii) SEQUENCE DESCRIPTION: SEQ ID NO:33:

Ser Asn Lys Thr Arg Ile Asp Glu Ala Asn
1               5                   10

Ala Arg Ala Thr Lys Met Leu
            15

(2) INFORMATION FOR SEQ ID NO: 34:

(i) SEQUENCE CHARACTERISTICS:
           (A) LENGTH: 17 amino acids
           (B) TYPE: amino acid sequence
           (C) STRANDEDNESS: Single
           (D) TOPOLOGY: Linear (ix) FEATURE:
           (B) LOCATION: 11
           (D) OTHER INFORMATION: Xaa represents Abu, or 2-Aminobutyric
                Acid (ii) SEQUENCE DESCRIPTION: SEQ ID NO:34:

Ser Asn Lys Thr Arg Ile Asp Glu Ala Asn
1               5                   10

Xaa Arg Ala Thr Lys Met Leu
            15

(2) INFORMATION FOR SEQ ID NO: 35:

(i) SEQUENCE CHARACTERISTICS:
           (A) LENGTH: 17 amino acids
           (B) TYPE: amino acid sequence
           (C) STRANDEDNESS: Single
           (D) TOPOLOGY: Linear (ix) FEATURE:

(ii) SEQUENCE DESCRIPTION: SEQ ID NO:35:

Ser Asn Lys Thr Arg Ile Asp Glu Ala Ala
1               5                   10

Gln Arg Ala Thr Lys Met Leu
            15

(2) INFORMATION FOR SEQ ID NO: 36:

(i) SEQUENCE CHARACTERISTICS:
           (A) LENGTH: 17 amino acids
           (B) TYPE: amino acid sequence
           (C) STRANDEDNESS: Single
           (D) TOPOLOGY: Linear (ix) FEATURE:

(ii) SEQUENCE DESCRIPTION: SEQ ID NO:36:

Ser Asn Lys Thr Ala Ile Asp Glu Ala Asn
1               5                   10

Gln Arg Ala Thr Lys Met Leu
            15

(2) INFORMATION FOR SEQ ID NO: 37:

(i) SEQUENCE CHARACTERISTICS:
           (A) LENGTH: 17 amino acids
           (B) TYPE: amino acid sequence
           (C) STRANDEDNESS: Single
           (D) TOPOLOGY: Linear (ix) FEATURE:

(ii) SEQUENCE DESCRIPTION: SEQ ID NO:37:

Ser Asn Lys Thr Arg Ile Asp Glu Ala Asn
1               5                   10

Gln Arg Ala Thr Lys Met Leu
                15

(2) INFORMATION FOR SEQ ID NO: 38:

(i) SEQUENCE CHARACTERISTICS:
            (A) LENGTH: 15 amino acids
            (B) TYPE: amino acid sequence
            (C) STRANDEDNESS: Single
            (D) TOPOLOGY: Linear (ix) FEATURE:

(ii) SEQUENCE DESCRIPTION: SEQ ID NO:38:

Ser Asn Lys Thr Arg Ile Asp Glu Ala Asn
1               5                   10

Gln Arg Ala Thr Lys
                15

(2) INFORMATION FOR SEQ ID NO: 39:

(i) SEQUENCE CHARACTERISTICS:
            (A) LENGTH: 17 amino acids
            (B) TYPE: amino acid sequence
            (C) STRANDEDNESS: Single
            (D) TOPOLOGY: Linear (ix) FEATURE:

(ii) SEQUENCE DESCRIPTION: SEQ ID NO:39:

Ser Asn Lys Thr Arg Ile Asp Glu Ala Asn
1               5                   10

Gln Arg Cys Thr Lys Met Leu
                15

(2) INFORMATION FOR SEQ ID NO: 40:

(i) SEQUENCE CHARACTERISTICS:
            (A) LENGTH: 17 amino acids
            (B) TYPE: amino acid sequence
            (C) STRANDEDNESS: Single
            (D) TOPOLOGY: Linear (ix) FEATURE:

(ii) SEQUENCE DESCRIPTION: SEQ ID NO:40:

Ser Asn Lys Thr Arg Ile Asp Glu Ala Cys
1               5                   10

Gln Arg Cys Thr Lys Met Leu
                15

(2) INFORMATION FOR SEQ ID NO: 41:

(i) SEQUENCE CHARACTERISTICS:
            (A) LENGTH: 12 amino acids
            (B) TYPE: amino acid sequence
            (C) STRANDEDNESS: Single
            (D) TOPOLOGY: Linear (ix) FEATURE:

(ii) SEQUENCE DESCRIPTION: SEQ ID NO:41:

```
Ile Asp Glu Ala Asn Gln Arg Ala Thr Lys
1               5                   10

Met Leu
    12
```

(2) INFORMATION FOR SEQ ID NO: 42:

(i) SEQUENCE CHARACTERISTICS:
        (A) LENGTH: 17 amino acids
        (B) TYPE: amino acid sequence
        (C) STRANDEDNESS: Single
        (D) TOPOLOGY: Linear (ix) FEATURE:

(ii) SEQUENCE DESCRIPTION: SEQ ID NO:42:

```
Ser Asn Lys Thr Arg Ile Asp Glu Ala Asn
1               5                   10

Gln Arg Leu Thr Lys Met Leu
                15
```

(2) INFORMATION FOR SEQ ID NO: 43:

(i) SEQUENCE CHARACTERISTICS:
        (A) LENGTH: 17 amino acids
        (B) TYPE: amino acid sequence
        (C) STRANDEDNESS: Single
        (D) TOPOLOGY: Linear (ix) FEATURE:

(ii) SEQUENCE DESCRIPTION: SEQ ID NO:43:

```
Ser Asn Lys Thr Arg Ile Asp Glu Ala Asn
1               5                   10

Gln Lys Ala Thr Lys Met Leu
                15
```

(2) INFORMATION FOR SEQ ID NO: 44:

(i) SEQUENCE CHARACTERISTICS:
        (A) LENGTH: 17 amino acids
        (B) TYPE: amino acid sequence
        (C) STRANDEDNESS: Single
        (D) TOPOLOGY: Linear (ix) FEATURE:
        (B) LOCATION: 12
        (D) OTHER INFORMATION: Xaa represents 2-aminopentanoic acid or
            norvaline (ii) SEQUENCE DESCRIPTION: SEQ ID NO:44:

```
Ser Asn Lys Thr Arg Ile Asp Glu Ala Asn
1               5                   10

Gln Xaa Ala Thr Lys Met Leu
                15
```

(2) INFORMATION FOR SEQ ID NO: 45:

(i) SEQUENCE CHARACTERISTICS:
        (A) LENGTH: 17 amino acids
        (B) TYPE: amino acid sequence
        (C) STRANDEDNESS: Single
        (D) TOPOLOGY: Linear (ix) FEATURE:

(ii) SEQUENCE DESCRIPTION: SEQ ID NO:45:

```
Ser Asn Lys Thr Arg Ile Asp Glu Ala Asn
1               5                   10

Gln Ala Ala Thr Lys Met Leu
                15
```

(2) INFORMATION FOR SEQ ID NO: 46:

(i) SEQUENCE CHARACTERISTICS:
        (A) LENGTH: 17 amino acids
        (B) TYPE: amino acid sequence
        (C) STRANDEDNESS: Single
        (D) TOPOLOGY: Linear (ix) FEATURE:

(ii) SEQUENCE DESCRIPTION: SEQ ID NO:46:

```
Ser Asn Lys Thr Arg Ile Asp Glu Ala Gln
1               5                   10

Gln Arg Ala Thr Lys Met Leu
                15
```

(2) INFORMATION FOR SEQ ID NO: 47:

(i) SEQUENCE CHARACTERISTICS:
        (A) LENGTH: 17 amino acids
        (B) TYPE: amino acid sequence
        (C) STRANDEDNESS: Single
        (D) TOPOLOGY: Linear (ix) FEATURE:

(ii) SEQUENCE DESCRIPTION: SEQ ID NO:47:

```
Ser Asn Lys Thr Arg Ile Asp Glu Ala Asn
1               5                   10

Gln Cys Ala Thr Lys Met Leu
                15
```

(2) INFORMATION FOR SEQ ID NO: 48:

(i) SEQUENCE CHARACTERISTICS:
        (A) LENGTH: 17 amino acids
        (B) TYPE: amino acid sequence
        (C) STRANDEDNESS: Single
        (D) TOPOLOGY: Linear (ix) FEATURE:

(ii) SEQUENCE DESCRIPTION: SEQ ID NO:48:

```
Ser Asn Lys Thr Arg Ile Asp Glu Ala Asn
1               5                   10

Cys Arg Ala Thr Lys Met Leu
                15
```

(2) INFORMATION FOR SEQ ID NO: 49:

(i) SEQUENCE CHARACTERISTICS:
        (A) LENGTH: 16 amino acids
        (B) TYPE: amino acid sequence
        (C) STRANDEDNESS: Single
        (D) TOPOLOGY: Linear (ix) FEATURE:

(ii) SEQUENCE DESCRIPTION: SEQ ID NO:49:

```
Ser Asn Lys Thr Arg Ile Asp Glu Ala Asn
1               5                   10

Gln Arg Ala Thr Lys Met
```

-continued

15

(2) INFORMATION FOR SEQ ID NO: 50:

(i) SEQUENCE CHARACTERISTICS:
        (A) LENGTH: 17 amino acids
        (B) TYPE: amino acid sequence
        (C) STRANDEDNESS: Single
        (D) TOPOLOGY: Linear (ix) FEATURE:

(ii) SEQUENCE DESCRIPTION: SEQ ID NO:50:

Ser Asn Lys Thr Arg Ile Asn Glu Ala Asn
1               5                   10

Gln Arg Ala Thr Lys Met Leu
                15

(2) INFORMATION FOR SEQ ID NO: 51:

(i) SEQUENCE CHARACTERISTICS:
        (A) LENGTH: 16 amino acids
        (B) TYPE: amino acid sequence
        (C) STRANDEDNESS: Single
        (D) TOPOLOGY: Linear (ix) FEATURE:

(ii) SEQUENCE DESCRIPTION: SEQ ID NO:51:

Ser Asn Arg Thr Arg Ile Asp Glu Ala Asn
1               5                   10

Gln Arg Ala Thr Arg Met
                15

(2) INFORMATION FOR SEQ ID NO: 52:

(i) SEQUENCE CHARACTERISTICS:
        (A) LENGTH: 16 amino acids
        (B) TYPE: amino acid sequence
        (C) STRANDEDNESS: Single
        (D) TOPOLOGY: Linear (ix) FEATURE:
        (B) LOCATION: 16
        (D) OTHER INFORMATION: Xaa represents Nle, or Norleucine (ii) SEQUENCE DESCRIPTION: SEQ ID NO:52:

Ser Asn Arg Thr Arg Ile Asp Glu Ala Asn
1               5                   10

Gln Arg Ala Thr Arg Xaa
                15

(2) INFORMATION FOR SEQ ID NO: 53:

(i) SEQUENCE CHARACTERISTICS:
        (A) LENGTH: 16 amino acids
        (B) TYPE: amino acid sequence
        (C) STRANDEDNESS: Single
        (D) TOPOLOGY: Linear (ix) FEATURE:
        (B) LOCATION: 4
        (D) OTHER INFORMATION: Xaa represents Abu, or 2-Aminobutyric
            Acid, (ix) FEATURE:
        (B) LOCATION: 16
        (D) OTHER INFORMATION: Xaa represents Nle, or Norleucine (ii) SEQUENCE DESCRIPTION: SEQ ID NO:53:

```
Ser Asn Arg Xaa Arg Ile Asp Glu Ala Asn
1               5                   10

Gln Arg Ala Thr Arg Xaa
                15
```

(2) INFORMATION FOR SEQ ID NO: 54:

(i) SEQUENCE CHARACTERISTICS:
        (A) LENGTH: 16 amino acids
        (B) TYPE: amino acid sequence
        (C) STRANDEDNESS: Single
        (D) TOPOLOGY: Linear (ix) FEATURE:
        (B) LOCATION: 16
        (D) OTHER INFORMATION: Xaa represents Nle, or Norleucine (ii) SEQUENCE DESCRIPTION: SEQ ID NO:54:

```
Ser Asn Arg Thr Arg Ile Asp Glu Ala Asn
1               5                   10

Gln Arg Ala Thr Arg Xaa
                15
```

(2) INFORMATION FOR SEQ ID NO: 55:

(i) SEQUENCE CHARACTERISTICS:
        (A) LENGTH: 16 amino acids
        (B) TYPE: amino acid sequence
        (C) STRANDEDNESS: Single
        (D) TOPOLOGY: Linear (ix) FEATURE:
        (B) LOCATION: 8
        (D) OTHER INFORMATION: Xaa represents Abu, or 2-Aminobutyric
           Acid, (ix) FEATURE:
        (B) LOCATION: 16
        (D) OTHER INFORMATION: Xaa represents Nle, or Norleucine (ii) SEQUENCE DESCRIPTION: SEQ ID NO:55:

```
Ser Asn Arg Thr Arg Ile Asp Xaa Ala Asn
1               5                   10

Gln Arg Ala Thr Arg Xaa
                15
```

(2) INFORMATION FOR SEQ ID NO: 56:

(i) SEQUENCE CHARACTERISTICS:
        (A) LENGTH: 16 amino acids
        (B) TYPE: amino acid sequence
        (C) STRANDEDNESS: Single
        (D) TOPOLOGY: Linear (ix) FEATURE:
        (B) LOCATION: 4 and 8
        (D) OTHER INFORMATION: Xaa represents Abu, or 2-Aminobutyric
           Acid, (ix) FEATURE:
        (B) LOCATION: 16
        (D) OTHER INFORMATION: Xaa represents Nle, or Norleucine (ii) SEQUENCE DESCRIPTION: SEQ ID NO:56:

```
Ser Asn Arg Xaa Arg Ile Asp Xaa Ala Asn
1               5                   10

Gln Arg Ala Thr Arg Xaa
                15
```

ASSAY FOR THE PROTEOLYTIC ACTIVITY OF SEROTYPE A FROM CLOSTRIDIUM BOTULINUM

INTRODUCTION

Type A botulinum neurotoxin (botox A) is one of seven serologically distinct neurotoxins produced by various strains of the anaerobic, spore forming bacterium, *Clostridium botulinum*. Together with the structurally related neurotoxin from *Clostridium tetani*, they are among the most potent toxins known [Eisel et al. (1986) EMBO J. 5: 2495–2502; Nieman (1991) In: *Sourcebook of Bacterial Protein Toxins* (J. Alouf and J Freer, Eds.) pp. 303–348, Academic Press, New York; Simpson (1981) *Pharmacol. Rev.* 33: 155–188; Dolly (1992) In: *Handbook of Experimental Pharmacology* (H. Herken and F. Hucho, Eds.), pp. 681–717. Springer-Verlag, Berlin.] Nonetheless, these toxins have proven to be highly useful tools for research on the mechanisms of neurotransmitter release [Nieman (1991) *Trends Cell Biol.* 4: 179–185; Schiavo et al., (1994) *Cell Biol.* 5: 221–229] and have even been used as drugs in humans, to treat certain types of muscle dysfunctions [Jancovic and Brin (1992) *New Engl. J. Med.* 324: 1186–1194]. All references cited herein supra and infra are hereby incorporated in their entirety by reference thereto.

Recognition of a consensus zinc-binding motif, HEXXH, in each of the botulinum and tetanus toxins was soon followed by reports that these toxins were zinc endoproteinases, highly specific for intracellular proteins involved in neurotransmission [Jongeneel et al. (1989) *FEBS Lett.* 242: 211–214; Schiavo et al. (1992b) *EMBO J.* 11, 3577–3583; Schiavo et al. (1992a) *Nature* 359: 832–835; Schiavo et al. (1993) *J. Biol. Chem.* 268: 23784–23787; Blasi et al. (1993) *Nature* 365: 160–163; Yamasaki et al. (1994) *J. Biol. Chem.* 269: 12764–12772]. For example, botox B and tetanus neurotoxins both cleave the same peptide bond in the synaptic vesicle protein synaptobrevin (also called VAMP), while botox A and botox E both cleave the synaptosomal protein SNAP-25, albeit at different sites (Schiavo et al., 1992a, ibid., 1993, ibid.; Blasi et al., 1993, ibid.). Proteolytic cleavage incapacitates these proteins, preventing neurotransmitter release. Toxicity is therefore a consequence of clostridial neurotoxin endoproteinase activity.

In earlier work [Schmidt and Bostian, (1995) *J. Prot. Chem.* 14: 703–708], we found that a 17-amino acid peptide, corresponding to residues 187–203 of SNAP-25 [Oyler, et al., (1989) *J. Cell Biol.* 109: 3039–3052], could serve as a good substrate for the proteolytic activity of botox A. The peptide was cleaved by botox A at a single glutaminyl-arginine bond, corresponding to residues 197 and 198 of SNAP-25, confirming earlier reports on the enzymatic specificity of botox A in synaptosomal preparations. Extending the peptide to the carboxy-terminus of SNAP-25 (187–206) or including up to 40 residues (167–206) had no positive influence on the rate of hydrolysis, compared to that with the 17-residue peptide. Others have reported that tetanus neurotoxin and types B, D, and F botulinum neurotoxins hydrolyze synthetic peptides, but relatively large peptides (>34 residues) were required [Shone et al., (1993) *Eur. J. Biochem.* 217: 965–971; Foran et al., (1994) Biochemistry 33: 15365–15374; Yamasaki et al., 1994, ibid.; Cornille et al., (1994) *Eur. J. Biochem.* 222: 173–181; Shone and Roberts, (1994) *Eur. J. Biochem.* 225: 263–270].

Type A botulinum toxin is currently employed as a drug to treat a variety of human muscle dysfunction. Current methods for estimating botulinum neurotoxin concentrations are the mouse lethality assay [Siegel and Metzger (1979) *Appl. Environ. Microbiol.* 38: 606–611], and an antibody neutralization test [Siegel (1988) *J. Clin. Microbiol.* 26: 2351–2356]. Both require the use of animals, can take up to four days to complete, and are inherently inaccurate. Dosages are calculated on the basis of the mouse lethality bioassay. However, this is unsatisfactory, because both assays are lengthy, inherently inaccurate, and require the use of animals. Furthermore, different results can be obtained depending on which protocol was used. Comparison of different lots of toxin, or toxin prepared in different laboratories, is difficult. Since the clostridial neurotoxins are enzymes, it follows that preparations could be quantitated as with any other enzyme, by determining the rate of the reaction catalyzed by the preparation. For botox A, this can be done by HPLC separation and quantitation of substrate hydrolysis products [Schmidt and Bostian (1995) *J. Prot. Chem.* 14: 703–708].

In this application, we describe an enzymatic assay for the quantitation of type A botulinum toxin wherein botox A can be conveniently quantitated, standardized, and compared on the basis of specific enzymatic activities, as is commonly done for virtually all other enzymes. The assay does not require the use of animals and can be done in one hour or less since no separation of hydrolysis products is needed.

SUMMARY

The present invention relates to botox A substrate peptides and their structural requirements and modifications suitable for the determination of type A botulinum toxin enzymatic (proteolytic) activity in a label-based assay. The present assay allows, for the first time, different preparations of type A botulinum toxin to be conveniently quantitated, standardized, and compared on the basis of specific enzymatic activities.

After toxin-catalyzed hydrolysis of the peptide substrates, results are quantitated by the addition of a label, followed by measuring the amount of label. Assays are very sensitive (2 to 5 nanograms per milliliter toxin can be detected), are highly accurate (typical standard deviations of triplicate determinations are less than 5%), do not require prior separation of products, can be completed in one hour, and do not require the use of animals.

In contrast, the conventional method for estimating concentrations of botulinum toxins is the mouse lethality bioassay. This method is not universally standardized, can take up to four days to complete, is highly inaccurate, and obviously requires the use of animals. Since the lethality of botulinum toxin is a consequence of its proteolytic activity, the enzymatic toxin assay can replace the mouse lethality bioassay in many applications.

Therefore, it is one object of the present invention to provide substrate peptides for use in an assay for the determination of type A botulinum toxin enzymatic activity.

It is another object of the present invention to provide a method for detecting and measuring type A botulinum toxin enzymatic activity or measuring the lethality of type A botulinum in a sample. In addition, the method can be used for standardization of different lots of toxin, and tracking of toxin during production and purification of drugs or solutions which contain type A botulinum toxin.

It is still a further object of the present invention to provide a method for screening compounds for type A botulinum inhibitory or stimulatory activity. The enzymatic assay described herein can be easily adapted to screen hundreds of compounds at once for toxin-inhibitory activity which can be further tested for effectiveness as anti-toxin drugs for treating a person with botulinum intoxication. Stimulatory compounds can be tested as drugs for treating an ever-expanding number of human muscle dysfunctions.

BRIEF DESCRIPTION OF THE DRAWINGS

These and other features, aspects, and advantages of the present invention will become better understood with regard to the following description, appended claims, and accompanying drawing where

DETAILED DESCRIPTION

Figure 1:
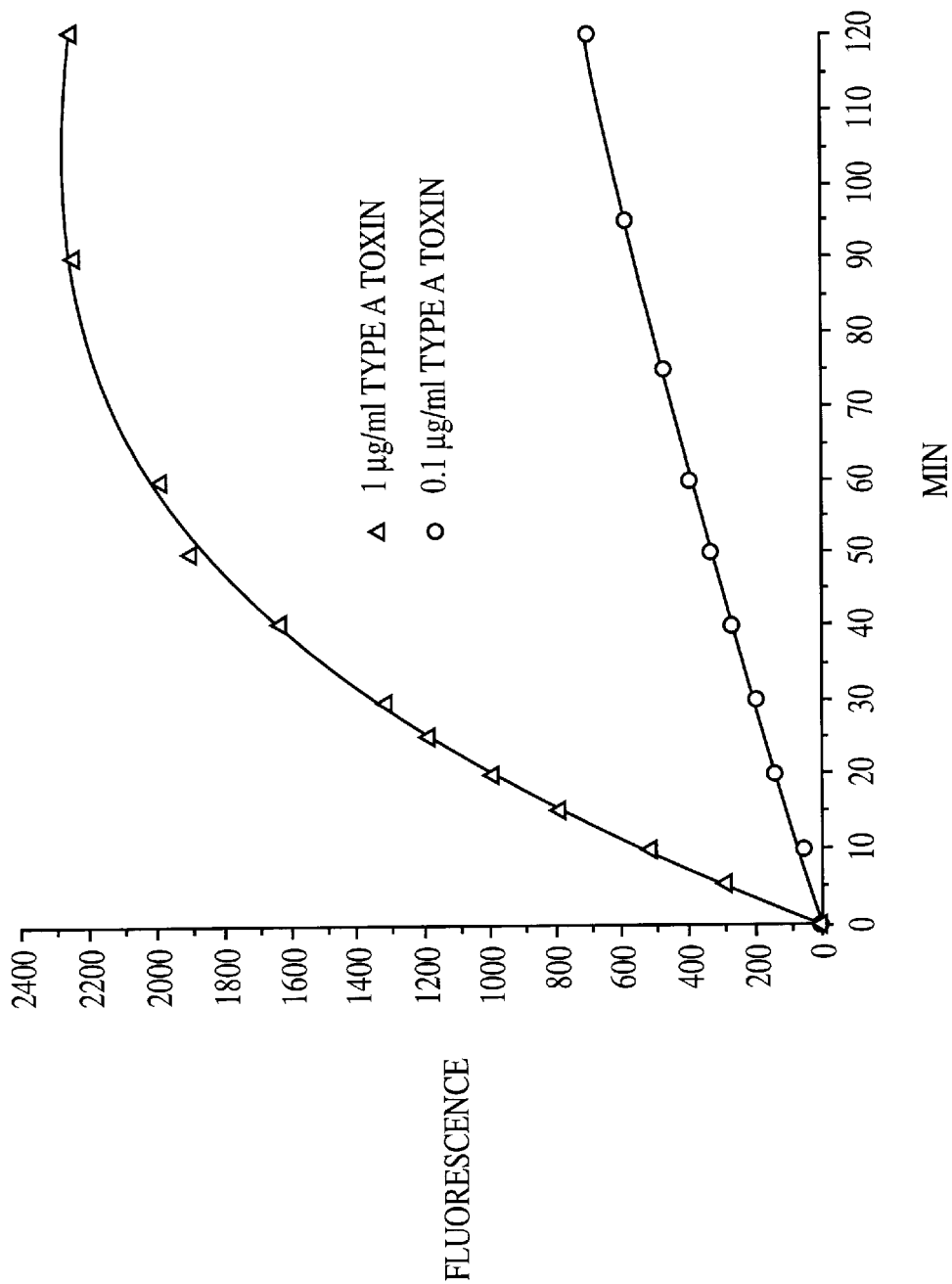
FIG. 1 represents the hydrolysis of 1 mM peptide 5, catalyzed by botox A. At the indicate times, aliquots of 20 μl were removed and reacted with fluorescamine, as described in the Materials and Methods below.

The present invention relates partially to peptides for use in an assay for the determination of type A botulinum toxin enzymatic (proteolytic) activity in a sample. Samples include, but are not limited to raw, cooked, or processed foods, beverages, animal feed, soil and water samples, pond sediments, lotions, and cosmetics, clinical drugs and solutions.

The assay of the present invention is based on the well-known fact that proteolytic cleavage of peptides or proteins results in production of new free amino groups. In this assay, type A botulinum toxin cleaves only one bond in the peptide substrate; therefore, one mole of free amino group results from each mole of peptide substrate that is hydrolyzed. The extent or rate of hydrolysis can be measured by determining the amount of, or rate of appearance of, free amino group. The concentration of toxin in an unknown sample can then be calculated, based on measurements of the extent or rate of hydrolysis effected by known concentrations of toxin.

In principle, any reagent that reacts with amino groups could be used as a label for this determination. However, in most cases the absorbance spectra of reactants and products are similar or identical. Therefore, a means of separating and identifying reactants and products must be developed and applied. Examples of reagents in this category are phenyl isothiocyanate and 2,4,6-trinitrobenzene-1-sulfonic acid.

Colorimetric reagents are commonly considered to be those which have no color, but which react with a certain substance or type of substance to give a colored product that is visible to the human eye. Quantitation involves measurement of the optical density of the solution with a spectrophotometer. For amino groups, a useful colorimetric reagent is ninhydrin, which reacts with primary amines to give a purple color (secondary amines yield a yellow color). However, it also reacts with ammonia, which is present in most solutions, unless great pains are taken to exclude or remove it. Therefore, chromatographic separation of products is necessary to avoid high background readings, which would compromise sensitivity.

Fluorescent reagents that react with primary and secondary amines include 5-dimethylaminonaphthalene-1-sulfonyl chloride, 4-dimethylaminoazobenzene-4'-sulfonyl chloride, and 4-N,N-dimethylaminoazobenzene 4'-isothiocyanate. However, these reagents are fluorescent even before reaction with amino groups, necessitating the separation of products from unreacted reagents which is time consuming and requires expensive equipment.

Another commonly-used reagent for detection and quantitation of amino groups is o-phthalaldehyde (OPA). This compound is not fluorescent, but forms fluorescent derivatives upon reaction with primary amines. Unfortunately, it also reacts strongly with ammonia, leading to high background readings.

If an assay for the proteolytic activity of type A botulinum toxin includes steps designed to separate products before quantitation (for example, see Schmidt and Bostian, 1995, ibid.), then most of the above-mentioned reagents could be used. Resolution of products could be accomplished by such techniques as high-pressure liquid chromatography (hplc), microbore or capillary liquid chromatography, or capillary electrophoresis. These add both time (methods development, validation, turnaround time, etc.) and significant expense (equipment purchase, maintenance, personnel training, etc.) to the procedure.

In the assay of the present invention, fluorescamine is used as the detection reagent because: (a), it is not fluorescent; (b), it reacts with amino groups to give intensely fluorescent compounds; and (c), it does not react with ammonia. These properties have made fluorescamine the reagent of choice in protease assays for many years. Nonetheless, fluorescamine will react with the native-sequence substrate peptide, due to the presence of two amino groups. We have developed a set of peptides containing modified sequences which do not react with fluorescamine, but are good substrates for the proteolytic activity of type A botulinum neurotoxin. Thus, the requirement for expensive and time-consuming product separation has been completely eliminated. Only a relatively inexpensive fluorimeter is needed.

In this context, in earlier work [Schmidt and Bostian (1995) ibid.], we found that a 17-amino acid peptide, S N K T R I D E A N Q R A T K M L, (SEQ ID NO:1), corresponding to residues 187–203 of SNAP-25 could serve as a good substrate for the proteolytic activity of botox A. However, this peptide is not suitable for use in the assay system described herein, because it reacts with labeling reagents to produce derivatives, and in the case of a fluoregenic label, a fluorescent derivative can seriously compromise the assay. The same can be said for larger peptides based on the SNAP-25 sequence, and for intact SNAP-25. This is due to the presence of the alpha-amino group of the N-terminal residue, and the epsilon-amino groups of the lysine residues at positions 3 and 15 in the sequence. This very high "background" fluorescence must be subtracted from that obtained in an assay, which severely compromises the sensitivity. Alternatively, the assay components and products must be separated from one another before quantitation, as described above, by procedures which are lengthy and require the use of very expensive, and specialized equipment.

Two changes were introduced to reduce or eliminate the reactivity of intact substrate with labeling or detection reagents: (1) acetylation of the alpha-amino group of the N-terminal residue; and (2) replacement of both lysines with arginines. With these changes, the "background" signal is typically less than 10% of the total in an assay. Therefore, it is not necessary to separate assay components and products before quantitation.

The amino acid sequences of the substrate peptides described in this invention are given below. In each case, the N-terminal amino group is acetylated, and the C-terminus is a carboxamide instead of a free carboxy group. This improves substrate properties; that is, they are hydrolyzed by type A toxin more rapidly than substrate peptides with free COOH at the C-termini. (see Schmidt and Bostian, 1995, ibid.). Acetylation of amino-terminal residues is a common practice in synthetic peptide chemistry. In our case, it was done to eliminate a free amino group that would otherwise react with fluorescamine. Some of the substrate peptides of the present invention are as follows:

| | | |
|---|---|---|
| 1. S N R T R I D E A N Q R A T R M L | (SEQ ID NO:2) |
| 2. S N R T R I D Q A N Q R A T R M L | (SEQ ID NO:3) |
| 3. S N R B R I D E A N Q R A T R M L | (SEQ ID NO:4) |
| 4. S N R T R I D E A N Q R A B R M L | (SEQ ID NO:5) |
| 5. S N R T R I D E A N Q R A T R X L | (SEQ ID NO:6) |
| 6. S N R B R I D E A N Q R A T R M | (SEQ ID NO:7) |
| 7. S N R B R I D Q A N Q R A T R M L | (SEQ ID NO:8) |
| 8. S N R B R I D Q A N Q R A T R M | (SEQ ID NO:9) |
| 9. S N R B R I D B A N Q R A T R M L | (SEQ ID NO:10) |
| 10. S N R B R I D B A N Q R A T R M | (SEQ ID NO:11) |
| 11. S N R T R I D Q A N Q R A T R M | (SEQ ID NO:12) |
| 12. S N R T R I D B A N Q R A T R M | (SEQ ID NO:13) |
| 13. S N R T R I D B A N Q R A T R M L | (SEQ ID NO:14) |

14. Any substrate peptide containing one or more of the residue changes shown in peptides 2 to 5, inclusive, with respect to peptide 1, and/or deletion of the carboxy-terminal leucine residue, and/or addition of more amino acids to the carboxy-terminal end, and/or addition of more amino acids to the amino-terminal end, and/or deletion of one or more amino acids from the amino-terminal end. For example the peptide S N R B R I D Q A N Q R A B R X L (SEQ ID NO: 15) would include many of the changes.

15. Any substrate peptide, for type A botulinum toxin, containing modified lysine residues, such as N (epsilon)-acetyl-lysine.

16. Any peptide that will serve as a substrate for type A botulinum toxin, but will not react with labeling reagents.

Abbreviations for the amino acids are:

| | |
|---|---|
| A | Alanine |
| B | 2-Aminobutyric acid |
| D | Aspartic acid |
| E | Glutamic acid |
| I | Isoleucine |
| K | Lysine |
| L | Leucine |
| M | Methionine |
| N | Asparagine |
| Q | Glutamine |
| R | Arginine |
| S | Serine |
| T | Threonine |
| X | 2-Aminohexanoic acid (norleucine) |

All the peptides described above can be used in a proteolytic assay to measure type A botulinum enzyme. Such an assay is performed as follows. One of the substrate peptides of the present invention is mixed with type A botulinum toxin. Typical concentrations are about 0.001 M peptide and about 0.01–1 microgram per ml toxin. The mixture also contains zinc chloride or zinc acetate at about 0.0002–0.0005 M. Zinc ion is added, because without it, the rate of catalysis by type A toxin is very low. The range specified is that which is most effective. Lower concentrations are insufficient, while higher concentrations are inhibitory (see Schmidt and Bostian, 1995, ibid.). Other salts of zinc could be used, provided that they are soluble. It is also possible that other divalent cations could be substituted for zinc.

Acetylated bovine serum albumin is present in the reaction solution at about 0.5–2.0 milligrams per ml, and a reducing agent, preferably dithiothreitol, at about 0.002–0.01 M. Assay volumes are usually about 15–60 microliters. The mixture is incubated at about 20–37° C. for a suitable period of time, usually about 5–60 minutes. Incubation (assay) endpoint is a function of the toxin (enzyme) concentration. In order to calculate an accurate initial rate of hydrolysis, it is necessary to stop the reaction before more than about 25% of the substrate is cleaved. Alternatively, the extent of hydrolysis at multiple time points can be determined, and the initial rate of hydrolysis is then calculated by extrapolation to zero- or near zero-time. These are standard procedures in enzymology well known to a person with ordinary skill in the art.

The reaction is stopped by addition of about 0.5–1.0 M sodium borate, pH 9.0–9.5, containing about 0.01 M iodoacetamide or sodium iodoacetate. In order to maximize fluorescent yield, measurements are done at pH 9.0–9.5 (common practice in fluorimetry). Sodium iodoacetate or iodoacetamide is added to eliminate reducing agent (dithiothreitol) in the assay mixture. If this is not done, the latter will react very rapidly with fluorescamine, and prevent its reaction with amino groups. Other possibilities include 4-vinylpyridine and N-ethylmaleimide.

After about 30 minutes at room temperature (typically about 18–23° C.), a fluorigenic reagent or other labeling reagent is added, that reacts with free amino groups to produce or fluorescent or other detectable derivative. Fluorescamine can be used at about 0.5–1.0 milligrams per ml in dimethylformamide. This is added with immediate and vigorous mixing. The fluorescence yield is then measured in a fluorimeter.

Hydrolysis of these peptides, catalyzed by type A botulinum neurotoxin, occurs between the glutaminyl-arginyl peptide bond that is found in each peptide. Quantitation can be achieved by comparing the fluorescence yield of the above-described assay with that obtained from known concentrations of a peptide representing the C-terminal product of the hydrolysis reaction. For example, if substrate peptide number 1 is used in the assay, then the appropriate C-terminal product peptide is: RATRML (residues 12–17 of SEQ ID NO: 2). The objective is to correlate fluorescence readings with the extent of hydrolysis. That is, if the substrate peptide is incubated with type A toxin for a period of time, then the reaction mixture is processed as described, and a fluorescence reading of 1250 is obtained, how many moles of substrate were cleaved during that time? Before this question can be answered, one must know the fluorescence yield per mole of C-terminal product. The simplest way to determine this is to synthesize the C-terminal product, then react known quantities of it with fluorescamine in the same way that it's done in an assay. Then, the fluorescence yield per mole of product can be calculated. The reaction rate can be expressed in standard terms, such as moles of substrate hydrolyzed (or products formed) per unit of time per mole (or mass) of enzyme (toxin). Using known concentrations of purified toxin, the hydrolysis rates for the peptides, per unit of toxin, can be calculated. These results can then be used to determine concentrations of toxin in preparations where the latter is unknown.

In other words, since type A botulinum toxin is an enzyme (a protease), it follows that concentrations of toxin in samples can be determined by measuring the amount of enzyme activity present, after the specific activity of the toxin is determined. For many enzymes, specific activity is expressed as micromoles of substrate transformed per minute per milligram of enzyme, or $\mu$mole/min/$\mu$g. Using the assay techniques described in this disclosure, the specific activity of type A botulinum toxin can be obtained by measuring the rate of proteolysis of a particular substrate peptide, catalyzed by a known concentration of toxin. (Once the specific proteolytic activity of type A toxin is determined, it need not be re-determined each time an assay is performed). Toxin concentration in a test sample can then be calculated, by determining the rate at which the test sample cleaves the same substrate. For example, the specific activity of type A toxin against peptide 5 (in Table II below) was 21 μmol/min/mg, when the initial substrate concentration was 1.0 mM. Therefore, if the rate of hydrolysis of 1.0 mM peptide 5, catalyzed by a sample containing an unknown concentration of type A toxin in a total assay volume of 20 μL, is determined to be 0.00042 μmol/min, then the amount of enzyme (type A toxin) present was: 0.00042/21=0.00002 mg, at a concentration of 0.00002/0.02=0.001 mg/ml. Thus, the concentration of type A botulinum toxin can be determined in preparations (such as, for example, those intended for human clinical use), without doing mouse lethality assays.

The assay could be used to search for inhibitors of type A botulinum proteolytic activity. Peptides that are slowly hydrolyzed, or not at all, might be starting points for drug development.

Based on information in Schmidt and Bostian, 1995 (ibid.), the minimum functional substrate is likely to be:

T R I D E A N Q R A T R M (SEQ ID NO:16)

or

R I D E A N Q R A T R M (SEQ ID NO:17)

The peptides listed below have been grouped on the basis of performance as substrate and/or potential inhibitors. Included are all of the peptides synthesized and tested, and many which have not been synthesized. Categorization of the latter are based on experience and theory. Note that many of the peptides contain lysine, rendering them less than ideal for a fluorimetric assay. If these are used as substrates, then the best approach would be to separate the assay products by HPLC, microbore or capillary liquid chromatography, or capillary electrophoresis.

Group 1, excellent substrates

| 1 | 2 | 3 | 4 | 5 | 6 | 7 | 8 | 9 | 10 | 11 | 12 | 13 | 14 | 15 | 16 | 17 | |
|---|---|---|---|---|---|---|---|---|----|----|----|----|----|----|----|----|---|
| S | N | R | T | R | I | D | E | A | N | Q | R | A | T | R | M | L | SEQ ID NO:2 |
| S | N | R | B | R | I | D | E | A | N | Q | R | A | T | R | M | L | SEQ ID NO:4 |
| S | N | R | T | R | I | D | Q | A | N | Q | R | A | T | R | M | L | SEQ ID NO:3 |
| S | N | R | T | R | I | D | B | A | N | Q | R | A | T | R | M | L | SEQ ID NO:14 |
| S | N | R | B | R | I | D | Q | A | N | Q | R | A | T | R | M | L | SEQ ID NO:8 |
| S | N | R | B | R | I | D | B | A | N | Q | R | A | T | R | M | L | SEQ ID NO:10 |
| S | N | K | T | R | I | D | Q | A | N | Q | R | A | T | K | M | L | SEQ ID NO:18 |
| S | N | K | B | R | I | D | E | A | N | Q | R | A | T | K | M | L | SEQ ID NO:19 |
| S | N | K | T | R | I | D | B | A | N | Q | R | A | T | K | M | L | SEQ ID NO:20 |
| S | N | K | B | R | I | D | Q | A | N | Q | R | A | T | K | M | L | SEQ ID NO:21 |
| S | N | K | B | R | I | D | B | A | N | Q | R | A | T | K | M | L | SEQ ID NO:22 |

Any of the above peptides, with residue 6=L
Any of the above peptides, with residue 17 (L) deleted, with or without the K/R substitutions described below
Any of the above peptides, with residue 3=K and simultaneously residue 15=R
Any of the above peptides, with residue 3=R and simultaneously residue 15=K Group 2, good substrates

| 1 | 2 | 3 | 4 | 5 | 6 | 7 | 8 | 9 | 10 | 11 | 12 | 13 | 14 | 15 | 16 | 17 | |
|---|---|---|---|---|---|---|---|---|----|----|----|----|----|----|----|----|---|
| S | N | R | S | R | I | D | E | A | N | Q | R | A | T | R | M | L | SEQ ID NO:23 |
| S | N | K | T | R | I | D | E | A | N | Q | R | A | T | K | M | L | SEQ ID NO:1 |
| S | N | K | T | R | I | D | E | A | N | Q | R | A | T | K | X | L | SEQ ID NO:24 |
| S | N | K | T | R | I | D | E | A | N | Q | R | A | B | K | M | L | SEQ ID NO:25 |
| S | N | K | T | R | I | D | E | A | N | Q | R | A | C | K | M | L | SEQ ID NO:26 |
| S | N | K | T | R | I | D | E | A | N | Q | R | B | T | K | M | L | SEQ ID NO:27 |

Any of the above peptides, with residue 6=L
Any of the above peptides, with residue 17 (L) deleted, with or without the K/R substitutions described below
Any of the above peptides, with residue 3=K and simultaneously residue 15=R
Any of the above peptides, with residue 3=R and simultaneously residue 15=R
Any of the above peptides, with residue 3=R and simultaneously residue 15=K Group 3, fair substrates

| 1 | 2 | 3 | 4 | 5 | 6 | 7 | 8 | 9 | 10 | 11 | 12 | 13 | 14 | 15 | 16 | 17 | |
|---|---|---|---|---|---|---|---|---|---|---|---|---|---|---|---|---|---|
| S | N | K | T | R | I | D | E | A | N | Q | R | A | T | K | A | L | SEQ ID NO:28 |
| S | N | K | T | R | I | D | E | A | N | N | R | A | T | K | M | L | SEQ ID NO:29 |
| S | N | K | T | R | I | D | E | B | N | Q | R | A | T | K | M | L | SEQ ID NO:30 |

Any of the above peptides, with residue 6=L
Any of the above peptides, with residue 17 (L) deleted, with or without the K/R substitutions described below
Any of the above peptides, with residue 3=K and simultaneously residue 15=R
Any of the above peptides, with residue 3=R and simultaneously residue 15=R
Any of the above peptides, with residue 3=R and simultaneously residue 15=K
Any of the above peptides, with one or more residues 1, 2, and/or 3 deleted
Group 4, poor substrates

| 1 | 2 | 3 | 4 | 5 | 6 | 7 | 8 | 9 | 10 | 11 | 12 | 13 | 14 | 15 | 16 | 17 | |
|---|---|---|---|---|---|---|---|---|---|---|---|---|---|---|---|---|---|
| S | N | K | T | R | I | D | E | A | N | Q | R | A | T | A | M | L | SEQ ID NO:31 |
| S | N | K | T | R | I | D | E | A | N | Q | R | A | S | K | M | L | SEQ ID NO:32 |
| S | N | K | T | R | I | D | E | A | N | A | R | A | T | K | M | L | SEQ ID NO:33 |
| S | N | K | T | R | I | D | E | A | N | B | R | A | T | K | M | L | SEQ ID NO:34 |
| S | N | K | T | R | I | D | E | A | A | Q | R | A | T | K | M | L | SEQ ID NO:35 |
| S | N | K | T | A | I | D | E | A | N | Q | R | A | T | K | M | L | SEQ ID NO:36 |
| S | N | K | T | R | I | D | E | A | N | Q | R | A | T | K | M | L | SEQ ID NO:37 |
| S | N | K | T | R | I | D | E | A | N | Q | R | A | T | K |   |   | SEQ ID NO:38 |
| S | N | K | T | R | I | D | E | A | N | Q | R | C | T | K | M | L | SEQ ID NO:39 |
| S | N | K | T | R | I | D | E | A | C | Q | R | C | T | K | M | L | SEQ ID NO:40 |

Any of the above peptides, with residue 6=L
Any of the above peptides, with more than one of the above-listed substitutions or deletions
Any of the above peptides, with residue 3=K and simultaneously residue 15=R
Any of the above peptides, with residue 3=R and simultaneously residue 15=R
Any of the above peptides, with residue 3=R and simultaneously residue 15=K
Group 5, very poor substrates or non-substrates; potential inhibitors (starting points for possible anti-toxin drug development).

| 1 | 2 | 3 | 4 | 5 | 6 | 7 | 8 | 9 | 10 | 11 | 12 | 13 | 14 | 15 | 16 | 17 | |
|---|---|---|---|---|---|---|---|---|---|---|---|---|---|---|---|---|---|
|   |   |   |   |   | I | D | E | A | N | Q | R | A | T | K | M | L | SEQ ID.NO:41 |
| S | N | K | T | R | I | D | E | A | N | Q | R | L | T | K | M | L | SEQ ID NO:42 |
| S | N | K | T | R | I | D | E | A | N | Q | K | A | T | K | M | L | SEQ ID NO:43 |
| S | N | K | T | R | I | D | E | A | N | Q | Z | A | T | K | M | L | SEQ ID NO:44 |
| S | N | K | T | R | I | D | E | A | N | Q | A | A | T | K | M | L | SEQ ID NO:45 |
| S | N | K | T | R | I | D | E | A | Q | Q | R | A | T | K | M | L | SEQ ID NO:46 |
| S | N | K | T | R | I | D | E | A | N | Q | C | A | T | K | M | L | SEQ ID NO:47 |
| S | N | K | T | R | I | D | E | A | N | C | R | A | T | K | M | L | SEQ ID NO:48 |

Any of the above peptides, with residue 6=L

Any of the above peptides, with more than one of the above-listed substitutions or deletions Any of the above peptides, with residue 3=K and simultaneously residue 15=R Any of the above peptides, with residue 3=R and simultaneously residue 15=R Any of the above peptides, with residue 3=R and simultaneously residue 15=K It is clear from the above groupings that a very large number of changes could be made, without total elimination of substrate properties.

Peptides can be made with commercially available automated synthesizers, using reagents and protocols obtained from the manufacturers. In most cases, solid-phase synthesis can be employed, where the C-terminal residue is covalently attached to an insoluble resin. Subsequent amino acids are then attached, one at a time. Amino acids can be obtained in chemically-modified ("protected") forms, designed so that they will react with the free amino group of the preceding residue in the peptide chain, but not with themselves. Upon completion of synthesis, the peptide is cleaved from the resin, protecting groups are removed, and the product is purified. These preparation protocols and others are well within the skill of a person in the art.

In another embodiment, the present invention relates to a kit for measuring botulinum neurotoxin type A in a sample. The kit will contain in close confinement, in a box for example, containers or vials containing a peptide substrate. Any of the peptide substrates can be used, preferably a peptide substrate from group 1 above. The kit will also include a control for use as a standard for the measurement of botox A. The control can be a known amount of botox A, or alternatively, a known amount of the C-terminal product corresponding to the peptide substrate chosen, as described above. The kit should also include a label able to detect a free amino group such that the products of hydrolysis of the peptide substrate (and the C-terminal control, if used) can be detected and measured. In addition, the kit can optionally have a container or containers with necessary buffers and cofactors for conducting the assay.

It is understood that these descriptions, examples and embodiments are for illustrative purposes only, and that various modifications would be suggested within the spirit and purview of this application and the scope of the appended claims.

The following examples are illustrative of the practice of the invention but should not be read as limiting the scope thereof.

The following materials and methods were used in the examples below.

MATERIALS AND METHODS

Reagents and Chemicals

BSA, fluorescamine, and hepes were obtained from Sigma Chemical Co., St. Louis, Mo. Acetylated BSA (AcBSA) was prepared by reaction of BSA with acetic anhydride, as described (Riordan and Vallee, 1967).

Peptide synthesis

Reagents

Peptides based on the amino acid sequence of SNAP-25 (Oyler et al., 1989) were synthesized and purified as described (Schmidt and Bostian, 1995, ibid.). All peptides were N-terminal acetylated, and had carboxamide instead of a free carboxy group at the C-terminus. Peptide nomenclature in this work differs from that in our previous report (Schmidt and Bostian, 1995). Here, peptides [1–15], [1–16], and [1–17] are native-sequence peptides, corresponding to residues 187–201, 187–202, and 187–203 of SNAP-25, respectively. For other peptides, names indicate the amino acid normally occupying that position, then its position number, then its replacement. For example, in peptide K15A, the native-sequence lysine at residue 15 is replaced by alanine.

The peptide synthesizer was a model 431A from Applied Biosystems, Foster City, Calif. We used "Fastmoc" protocols and chemicals obtained from the same company. Peptides were synthesized with carboxamide C-termini, by using the Rink amide resin from Calbiochem-Novabiochem, La Jolla, Calif. N-terminal alpha amino groups were acetylated. Purification was by reverse-phase HPLC, with various gradients of 0.1% TFA and acetonitrile. Peptides were collected from the columns, lyophililzed, dissolved in 2–4 ml water, and lyophilized again.

Botox A

Purified botox A was purchased from List Biological Laboratories, Campbell, Calif., and from the Food Research Institute, Madison, Wis. Upon sodium dodecyl sulfate-polyacrylamide gel electrophoresis under reducing conditions followed by staining with Coomassie Blue, each product exhibited a band for the toxin heavy chain (molecular mass about 100 kDa) and another for the toxin light chain (molecular mass about 50 kDa). No significant amounts of other proteins were visible. Toxin concentrations were estimated with the BCA protein assay (Pierce Chemical Co., Rockford, Ill.), with bovine serum albumin as the standard. For storage, toxin was equilibrated by dialysis with 0.05M hepes/0.15M NaCl, pH 7.3. BSA was added and toxin concentration was adjusted, such that the solution contained 2 mg/ml BSA and 0.02 mg/ml toxin. If the toxin was to be used in the fluorescamine assay, AcBSA was substituted for BSA. Preparations were then stored in small aliquots (20–40 $\mu$L) at $-70°$ C. Each aliquot was thawed and used only once. Typical assay conditions for botox A are described below. However, as with virtually any enzymatic assay, parameters such as preincubation time and temperature, assay time and temperature, type of buffer, buffer concentration, pH, and concentrations of reactants and additives (botox A, peptide substrate, DTT, $ZnCl_2$, BSA or AcBSA) can be altered to various extents, without completely eliminating botox A enzymatic activity.

HPLC Assay of Botox A Proteolytic Activity

Peptide substrate was weighed and dissolved in a volume of 20 mM hepes, pH 7.3, such that the substrate concentration was 2 mM. An aliquot of toxin (40 $\mu$L) was thawed and mixed with 360 $\mu$L of a solution (diluent) containing 2 mg/ml BSA or AcBSA, 10 mM DTT, 0.5 mM $ZnCl_2$, and 20 mM hepes, pH 7.3. Before addition of peptide substrate, this mixture was preincubated at 37° C. for 30 min. Reaction was initiated by mixing equal volumes of peptide with preincubated botox A. Assay tubes were incubated at 37° C. At time intervals (typically, 5–10 min apart), aliquots (usually 20 or 30 $\mu$L) were mixed with an equal volume of 2% TFA, to stop the reaction. Results were quantitated by HPLC as described (Schmidt and Bostian, 1995).

Fluorescamine Assay of Botox A Proteolytic Activity

Quantitation of proteolytic activity with fluorescamine was based on the procedures of Galen et al. (1978). Amino groups, produced by proteolytic cleavage of peptides, are reacted with fluorescamine to give fluorescent product. The amount of fluorescence is proportional to the extent of hydrolysis. Since BSA reacts strongly with fluorescamine, it was replaced by AcBSA in our fluorimetric assays. Use of AcBSA instead of BSA in fluorimetric assays was reported by Wang and Liang (1994). In that study, the protease was porcine renin.

After assays were stopped with TFA (see section 2.3), 0.7 ml of 0.5M sodium borate/10 mM iodoacetamide, pH 9.5, was added to each aliquot, then let stand at room temperature (18–23° C.) for 30 min. This step has two important effects: first, the pH is made alkaline, which enhances fluorescence yield (Galen et al., 1978), and second, iodoacetamide reacts with DTT to eliminate sulfhydryl groups. The latter must be done because sulfhydryl groups react very rapidly with fluorescamine and thereby prevent formation of fluorescent derivatives with amino groups. Finally, 0.1 ml of 1 mg/ml fluorescamine in dimethylformamide was added, with immediate vigorous mixing. Fluorescence was measured on a Perkin-Elmer model 650-40 fluorescence spectrophotometer. Excitation and emission wavelegths were 390 nm and 490 nm, respectively. In all assays, appropriate blanks were made by first mixing TFA with the peptide solution, then adding botox A. Fluorescence readings from these blanks (typically, 100 or less) were subtracted from the assay values.

Calculations

Kinetic parameters of the synthetic substrates were calculated from Lineweaver-Burk plots (Segel, 1975), with peptide concentrations ranging from 0.02 to 3.0 mM. Results are the averages of triplicate determinations, ± standard deviations. Where standard deviations are not shown, the range was ±10% or less.

RESULTS AND DISCUSSION

BSA Stimulation of Botox A Proteolysis

BSA accelerated the initial rate of botox A-catalyzed hydrolysis of peptide [1–17](data not shown). The highest stimulation was found at about 2 mg/ml BSA, with very similar results at 1 mg/ml. The concentration of BSA that produced half of the maximum effect was approximately 0.2 mg/ml (3 $\mu$M). In addition to peptide [1–17], similar results were found for several other peptide substrates (not shown). The three different preparations of BSA, of various degrees of purity (see Materials and Methods), stimulated to the same extent. Dialysis of the BSA did not alter the degree of stimulation. In control experiments, BSA alone had no effect on the substrate peptides, and botox A did not cleave BSA.

Human, horse, goat, sheep, and rabbit albumins also accelerated the hydrolysis of substrate peptides by botox A, but to a lesser extent than did BSA. Bovine gamma globulins, ovalbumin, lysozyme, ribonuclease, and gelatin had no effect, suggesting that the stimulation might be specific to serum albumins.

Kinetic analyses revealed that the increase in hydrolysis rate caused by BSA was primarily due to a tenfold increase in $k_{cat}$, while the $K_m$ decreased by a factor of three. Therefore, the catalytic step was more strongly affected than substrate binding. Furthermore, it is clear that the stimulatory effect of BSA was not simply due to stabilization of botox A, since assay times were brief (usually ten minutes) and botox A has been shown to be stable for several hours under assay conditions in the absence of BSA (Schmidt and Bostian, 1995, ibid.).

Substrate Requirements of Botox A

Analogs of peptide [1–17] were synthesized with various amino acids substituted for the native-sequence residues, to study the substrate requirements of botox A. In addition, peptides [1–15] and [1–16] were included, to examine the effects of substrate peptide length on the rate of catalysis, in the presence of BSA. Results are summarized in Table I.

In our earlier work, no hydrolysis was detected when peptide [1–15], representing residues 187–201 of SNAP-25, was incubated with botox A (Schmidt and Bostian, 1995). However, in this study, with BSA in the assay, a very slow rate of hydrolysis was found. Nonetheless, peptide [1–15] was a relatively poor substrate for botox A, and several lines of evidence suggest that this was due to a diminished catalytic rate, rather than a lower binding affinity for botox A. First, the estimated $k_{cat}$ of peptide [1–15] was only 2–3% of those for peptides [1–16] and [1–17], but the estimated $K_m$ implied good binding. Second, at peptide concentrations above 2 mM, the reaction rate decreased, relative to lower substrate concentrations, resulting in a non-linear Lineweaver-Burk plot (not shown). Third, peptide [1–15] inhibited hydrolsis of peptide [1–17] by 17%, when both were present at 1.0 mM. These findings demonstrated that peptide [1–15] can function as an inhibitor, as well as a substrate. Therefore, the low rate of peptide [1–15] hydrolysis was due to a decreased rate of catalysis, and not to a lack of binding.

Extending the peptide to 16 residues by adding methionine to the C-terminus produced an excellent substrate for the proteolytic activity of botox A. The $k_{cat}$ for peptide [1–16] is typical of substrates for many proteases and other enzymes. In contrast, the $K_m$ is relatively high, but similar to those reported for synthetic substrates of type B botulinum and tetanus neurotoxins (Cornille et al., 1994, ibid.; Foran et al., 1994, ibid.; Shone and Roberts, 1994, ibid.). Eliminating the first three residues (SNK) led to a 43% reduction in hydrolysis rate (not shown). Although this 13-residue peptide was still a good substrate, it was clear that of the tested peptides, the best substrate had 16 residues, with 11 on the amino-terminal side of the cleavage site, and five on the carboxy-terminal side.

TABLE I

Kinetic Parameters of Synthetic Peptides Tested as Substrates for Botox A

| Peptide | Sequence[1] | Relative rate[2] | $K_m$ (mM)[3] | $k_{cat}$ ($sec^{-1}$) | SEQ ID NO: |
|---|---|---|---|---|---|
| [1 - 15] | S N K T R I D E A N Q R A T K | 0.03 | (0.9) | (1.0) | SEQ ID NO:38 |
| [1 - 16] | S N K T R I D E A N Q R A T K M | 1.17 | 1.6 ± 0.15 | 6 ± 4 | SEQ ID NO:49 |
| [1 - 17] | S N K T R I D E A N Q R A T K M L | 1.00 | 1.7 ± 0.1 | 47 ± 2 | SEQ ID NO:1 |
| M16A | S N K T R I D E A N Q R A T K A L | 0.38 | 1.9 ± 0.1 | 25 ± 1 | SEQ ID NO:28 |
| M16X | S N K T R I D E A N Q R A T K X L | 1.20 | 0.58 ± 0.02 | 30 ± 1 | SEQ ID NO:24 |
| K15A | S N K T R I D E A N Q R A T A M L | 0.12 | (1.0) | (8.0) | SEQ ID NO:31 |

TABLE I-continued Kinetic Parameters of Synthetic Peptides Tested as Substrates for Botox A

| Peptide | Sequence[1] | Relative rate[2] | $K_m$ (mM)[3] | $k_{cat}$ ($sec^{-1}$) | SEQ ID NO: |
|---|---|---|---|---|---|
| T14S | S N K T R I D E A N Q R A S K M L | 0.26 | (1.2) | (9.0) | SEQ ID NO:32 |
| T14B | S N K T R I D E A N Q R A B K M L | 1.20 | 1.3 ± 0.1 | 35 ± 2 | SEQ ID NO:25 |
| A13B | S N K T R I D E A N Q R B T K M L | 0.79 | 1.8 ± 0.1 | 39 ± 2 | SEQ ID NO:27 |
| A13L | S N K T R I D E A N Q R L T K M L | <0.02 | ND | ND | SEQ ID NO:42 |
| R12K | S N K T R I D E A N Q K A T K M L | <0.02 | ND | ND | SEQ ID NO:43 |
| R12Z | S N K T R I D E A N Q Z A T K M L | <0.02 | ND | ND | SEQ ID NO:44 |
| R12A | S N K T R I D E A N Q A A T K M L | <0.02 | ND | ND | SEQ ID NO:45 |
| Q11A | S N K T R I D E A N A R A T K M L | 0.19 | ND | ND | SEQ ID NO:33 |
| Q11B | S N K T R I D E A N B R A T K M L | 0.25 | 0.83 ± 0.05 | 7.7 ± 0.2 | SEQ ID NO:34 |
| Q11N | S N K T R I D E A N N R A T K M L | 0.66 | 0.75 ± 0.08 | 19 ± 3 | SEQ ID NO:29 |
| N10Q | S N K T R I D E A Q Q R A T K M L | <0.02 | ND | ND | SEQ ID NO:46 |
| N10A | S N K T R I D E A A Q R A T K M L | 0.06 | 0.60 ± 0.03 | 1.8 ± 0.1 | SEQ ID NO:35 |
| A9B | S N K T R I D E B N Q R A T K M L | 0.38 | 1.1 ± 0.1 | 11 ± 1 | SEQ ID NO:30 |
| E8Q | S N K T R I D Q A N Q R A T K M L | 2.08 | 0.75 ± 0.04 | 51 ± 3 | SEQ ID NO:18 |
| D7N | S N K T R I N E A N Q R A T K M L | 0.23 | 0.82 ± 0.06 | 5.0 ± 0.3 | SEQ ID NO:50 |

[1]Non-standard amino acid abbreviations are: B, 2-aminobutyric acid; X, 2-aminohexanoic acid (norleucine); and Z, 2-aminopentanoic acid (norvaline).
[2]Initial hydrolysis rates relative to peptide [1 - 17]. Peptide concentrations were 1.0 mM.
[3]Numbers in parentheses wereestimated from plots of initial rates vs. substrate concentrations (peptides [1 - 15] and K15A), or from the four lowest substrate concentrations on the Lineweaver-Burk plot (T14S). ND: not determined.

Adding leucine, i.e. peptide [1–17], had little effect on kinetic constants. Nonetheless, leucine was retained in subsequent peptides, because it improved the HPLC characteristics of the C-terminal hydrolysis product.

Peptides M16A and M16X were synthesized to test the importance of having methionine, in particular, as residue 16. M16A was still a substrate, in spite of this relatively drastic amino acid change, although the $k_{cat}$ decreased by almost 50%. In peptide M16X, norleucine can be considered an analog of methionine, with a methylene group in place of the sulfur. This peptide was a good substrate, and was hydrolyzed somewhat faster than the native-sequence peptide at 1.0 mM, due to its lower $K_m$. In sum, although residue 16 was required for efficient cleavage by botox A, it did not need to be methionine.

Peptides K15A and T14S exhibited kinetics similar to those of peptide [1–15]. A significantly lower hydrolysis rate was found, compared to peptide [1–17], and estimates of kinetic constants indicated that the main effect was on the rate of catalysis. Moreover, initial velocities decreased at peptide concentrations above 2 mM, suggesting that K15A and T14S can function as inhibitors as well as substrates. Lineweaver-Burk plots were clearly non-linear and for peptide T14S the deviation from linearity is most noticeable at higher substrate concentrations. However, by using only the four lowest substrate concentrations, we calculated a $K_m$ of 1.2 mM and a $k_{cat}$ of 9.0 $sec^{-1}$.

In peptide T14S, the side-chain methyl group of threonine is eliminated, but the hydroxyl group is retained. In T14B, the opposite situation occurs. In contrast to T14S, peptide T14B is a good substrate for botox A and gave typical Michaelis-Menten kinetics with constants similar to those of the native sequence peptides. Therefore, it is clear that the hydrophobic methyl group is preferred by the enzyme at this residue, rather than the hydrophilic hydroxyl group.

Replacing alanine with 2-aminobutyric acid at residue 13 (peptide A13B) had very little effect, but substitution with the branched amino acid, leucine, caused the rate of hydrolysis to drop below the limits of detection. Furthermore, this peptide (A13L) inhibited hydrolysis of peptide [1–17] by 30%, when both were present at 1.0 mM. Preliminary results (not shown) indicated a Ki of about 1–2 mM for A13L. These findings suggest that the binding affinity of A13L is similar to that of peptide [1–17], but the net rate of catalysis is greatly diminished.

Residues 11 (glutamine) and 12 (arginine) represent the P1 and P1' residues, respectively, at the site of botox A-catalyzed peptide hydrolysis (substrate terminology as defined by Schechter and Berger (1967) *Biochem. Biophys. Res. Comm.* 27: 157–162). Replacing the P1 glutamine with alanine (Q11A), 2-aminobutyric acid (Q11B), or asparagine (Q11N) slowed but did not eliminate hydrolysis. For Q11B and Q11N, this was due to a decreased rate of catalysis and not to diminished binding, since Km values for these peptides were actually lower than for the native-sequence peptides, [1–16] and [1–17]. In contrast, replacing the P1' arginine with lysine, norvaline, or alanine eliminated detectable hydrolysis. Therefore, the P1' residue is probably more important than the P1 for substrate recognition and cleavage by botox A.

The rate of hydrolysis was also strongly affected by amino acid substitutions at residue 10, the P2 site. No hydrolysis of peptide N10Q was detected, although this is a relatively conservative change. Peptide N10A, wherein the carboxamide side chain of asparagine was eliminated, was only very slowly cleaved. For N10A, the $K_m$ indicated that substrate binding was somewhat stronger than in the native-sequence peptides, but the $k_{cat}$ was only about 4% of that for peptide [1–17]. Peptide N10A inhibited hydrolysis of [1–17] by 30% when both were present at 1.0 mM.

In the native sequence, alanine is the P3 residue. Substitution with 2-aminobutyric acid (peptide A9B) lengthened the side chain by one methylene group. This peptide was still a good substrate at 1.0 mM, with a $K_m$ slightly lower than that of peptide [1–17], but the $k_{cat}$ was reduced by about 75%. Although other changes to this residue have not been synthesized, it is likely that a relatively small, uncharged residue is preferred at this location.

Glutamic acid at the P4 site is one of only two acidic residues in the substrate, compared to four basic residues. We investigated the requirement for a negative charge at this location by substituting with glutamine. Interestingly, this led to a doubling of the rate of hydrolysis at 1.0 mM, compared to that for peptide [1–17]. Kinetic analysis revealed that this was due to a decrease in $K_m$ by about 50%, while $K_{cat}$ was unchanged. Thus, in assays at concentrations below the $K_m$ of peptide [1–17], peptide E8Q appears to be the better substrate.

In contrast, eliminating the negative charge at the P5 site, by substituting asparagine for aspartic acid (peptide D7N), led to a substantial decrease in catalytic rate. Although the $K_m$ suggests good binding of D7N to botox A, the $k_{cat}$ was only about 10% of that for peptide [1–17]. In sum, these observations show that in the botox A substrate peptides, a negative charge is preferred at the P5 site, but not at the P4 site.

Peptide Substrates for Botox A Proteolytic Activity

In earlier work, using HPLC to separate and quantitate substrate and products of proteolytic cleavage, we found that botox A could catalyze the hydrolysis of a 17-residue peptide (Schmidt and Bostian, 1995). Although the alpha-amino group of this peptide was acetylated, it contained two free amino groups, due to the presence of two lysine residues at positions 3 and 15 in the sequence. In order to use fluorescamine detection to quantitate the enzymatic activity of botox A without separation of products, the two amino groups would have to be eliminated from the substrate. Otherwise, fluorescence resulting from reaction of fluorescamine with these groups would be twice that of the maximum that could be expected from 100% cleavage of substrate, seriously compromising the sensitivity of the assay.

In the substrate peptide, replacement of lysine-15 or lysine-3 (Schmidt and Bostian, unpublished result) with alanine led to substantial decreases (82–88%) in the rate of botox A-catalyzed hydrolysis, suggesting that positively-charged residues were required at these sites. Therefore, peptides were synthesized with arginine as replacement for both lysines. The modified peptides were tested as substrates for botox A, with 1 mg/ml BSA in the assays, by comparing initial rates of hydrolyses to that of the native-sequence peptide. Results were quantitated by the HPLC assay, and are shown in Table II.

TABLE II

Initial hydrolysis of peptide substrates catalyzed by Botox A.

| | Peptide Sequence/SEQ ID NO: | Rate | Relative Rate* |
|---|---|---|---|
| 1 | S N K T R I D E A N Q R A T K M L/1 | 7.6 ± 0.3 | 1.0 |
| 2 | S N R T R I D E A N Q R A T R M L/2 | 11.3 ± 0.5 | 1.5 |
| 3 | S N R B R I D E A N Q R A T R M L/4 | 15.8 ± 0.8 | 2.1 |
| 4 | S N R T R I D Q A N Q R A T R M L/3 | 12.6 ± 0.5 | 1.7 |
| 5 | S N R T R I D B A N Q R A T R M L/14 | 12.9 ± 0.3 | 1.7 |
| 6 | S N R B R I D B A N Q R A T R M L/10 | 25.3 ± 0.7 | 3.3 |
| 7 | S N R B R I D Q A N Q R A T R M L/8 | 14.1 ± 0.7 | 1.9 |

*Initial rate of peptide hydrolysis, in umoles/min/mg, with 1.0 mM peptide and 1 mg/ml BSA.

In Table II, peptide 1 is the native-sequence peptide, corresponding to residues 187–203 of the neuronal protein, SNAP-25 (Schmidt and Bostian, 1995; Oyler et al., 1989). Replacing both lysines with arginines (peptide 2) resulted in a substrate that was hydrolyzed by botox A slightly faster than peptide 1. Thus, it was possible to eliminate the two free amino groups from the peptide, without adverse effects on substrate properties. Other sequence modifications were also incorporated, based on earlier work, which suggested that such changes might result in enhanced hydrolysis rates. For example, peptide 6 was hydrolyzed more than three times faster than the native-sequence peptide 1.

Reaction of fluorescamine with 30 nmoles peptide 1, the amount present in a typical assay, gave intense fluorescence, above the range of the fluorimeter (>3000). However, reaction of fluorescamine with 30 nmoles peptide 2 resulted in very low fluorescence, 37±0. Peptides 3–7 gave similar results.

Effects of AcBSA on Substrate Kinetic Constants

As noted above, the presence of 1 mg/ml BSA greatly enhanced the rate of botox A-catalyzed peptide hydrolysis. However, reaction of fluorescamine with 30 μg BSA, the amount present in a typical assay, gave intense fluorescence, above the range of the fluorimeter (>3000). In contrast, reaction of 30 μg AcBSA gave a fluorescence of 31±1, suggesting that the latter could replace BSA in assays, when fluorescamine quantitation was employed. Therefore, it was necessary to compare the effects of AcBSA with those of BSA on the kinetic parameters of botox A-catalyzed proteolysis. Results are shown in Table III. With the exception of peptide 6, peptides exhibited higher initial hydrolysis rates in AcBSA than in BSA. Values for $k_{cat}$ were essentially unchanged (except for peptide 3), but $K_m$ values were lower, suggesting that AcBSA facilitates binding of substrate to botox A. In sum, it was clear that acetylation of BSA did not eliminate the positive effect of this protein on botox A-catalyzed hydrolysis rates. Indeed, a small enhancement was found.

TABLE III

Comparison of Kinetic Parameters of Botox A Substrates in BSA and AcBSA.

| Peptide[2] | Rate[1] | | $K_m$ (mM) | | $K_{cat}$ (sec$^{-1}$) | |
|---|---|---|---|---|---|---|
| | In BSA | In AcBSA | In BSA | In AcBSA | In BSA | In AcBSA |
| 1 | 8 | 10 | 1.7 | 0.59 | 47 | 41 |
| 2 | 11 | 16 | 1.4 | 0.53 | 68 | 61 |
| 3 | 16 | 18 | 0.91 | 0.32 | 75 | 58 |
| 4 | 13 | 19 | 0.76 | 0.47 | 64 | 68 |
| 5 | 13 | 21 | 0.74 | 0.33 | 69 | 70 |
| 6 | 24 | 25 | 0.52 | 0.40 | 89 | 86 |
| 7 | 14 | 22 | ND[3] | 0.31 | ND[3] | 73 |

[1]Initial rate of hydrolysis, in µmoles/min/mg, with 1.0 mM peptide.
[2]Peptide sequences as in Table II.
[3]ND: not determined.

Assay of Botox A Proteolytic Activity with Fluorescamine

Toxin that was stored in AcBSA, and diluent containing AcBSA, were used in these assays. The substrate was peptide 5, at an initial concentration of 1.0 mM. Aliquots of 20 µl were removed at time intervals, and processed as described in the Materials and Methods section. Results (FIG. 1) showed an increase in fluorescence with time, corresponding to botox A-catalyzed hydrolysis of the substrate (confirmed by HPLC analyses of parallel samples). Moreover, the reaction rate with 0.1 µg/ml botox A was approximately 10% of that for 1 µg/ml toxin; that is the rate was proportional to the concentration of botox A.

The fluorescence in FIG. 1 resulted from reaction of fluorescamine with the alpha amino group of the carboxy-terminal proteolysis product, peptide RATRML. Although peptide 5 was the substrate in this example, peptides 2 through 7 would all give the same fluorescence per mole of cleaved substrate, because the carboxy-terminal product is the same in all.

Assay sensitivity was tested by incubating 1.0 mM peptide 7 with concentrations of botox A ranging from 0.001 to 1 µg/ml, for 6 hr. Results are summarized in Table IV.

TABLE IV

| Fluorescence after substrate incubation with Botox A | | |
|---|---|---|
| Botox A (ug/ml) | Fluorescence (6 hrs)* | S/N** |
| 1 | 2378 ± 66 | 25.3 |
| 0.1 | 1402 ± 10 | 16.8 |
| 0.01 | 160 ± 16 | 3.0 |
| 0.001 | 11 ± 3 | 1.2 |

*Blank-corrected
**Signal to noise ratio, or assay fluorescence divided by the corresponding blank fluorescence.

It appears likely that a botox A concentration of 0.001 µg/ml represents the lower limit of sensitivity, while a more conservative estimate would place this limit at 0.01 µg/ml. Nonetheless, the assay can be used over a wide range of botox A concentrations.

What is claimed is:

1. A substrate peptide for determining the proteolytic acitivity of botulinum neurotoxin type A using fluorescamine detection without separation of products, said substrate peptide consisting of at least 16 residues of SEQ ID NO:1, wherein said peptide is modified by acetylating the N-terminal amino group and eliminating the negative charge at the carboxy terminus.

2. A method for measuring amount of botulinum neurotoxin type A in a sample suspected of containing botulinum neurotoxin type A, said method comprising:

(i) combining said sample with a substrate peptide according to claim 1 such that hydrolysis of said peptide is initiated;

(ii) stopping hydrolysis of said peptide at different time points;

(iii) measuring amount of hydrolysis at each time point by combining a detectable label able to detect free amino groups resulting from said hydrolysis; and (iv) comparing said measurements with amount of label produced from a known concentration of toxin measured under similar conditions.

3. The method of claim 2 wherein, said sample is selected from the group consisting of raw, cooked and processed foods.

4. The method of claim 2 wherein, said sample is a clinical solution for administering to a patient.

5. A method for measuring amount of botulinum neurotoxin type A in a sample suspected of containing botulinum neurotoxin type A, said method comprising:

(i) combining said sample with a substrate peptide according to claim 1 such that hydrolysis of said peptide is initiated;

(ii) stopping hydrolysis of said peptide at different time points;

(iii) measuring amount of hydrolysis at each time point by combining a detectable label able to detect free amino groups resulting from said hydrolysis; and (iv) comparing said measurements with amount of label produced from a known concentration of toxin measured under similar conditions wherein, said substrate peptide is selected from the group consisting of:

1. S N R T R I D E A N Q R A T R M L (SEQ ID NO:2)

2. S N R T R I D Q A N Q R A T R M L (SEQ ID NO:3)

3. S N R B R I D E A N Q R A T R M L (SEQ ID NO:4)

4. S N R T R I D E A N Q R A B R M L (SEQ ID NO:5)

5. S N R T R I D E A N Q R A T R X L (SEQ. ID NO:6)

6. S N R B R I D E A N Q R A T R M (SEQ ID NO:7)

7. S N R B R I D Q A N Q R A T R M L (SEQ ID NO:8)

8. S N R B R I D Q A N Q R A T R M (SEQ ID NO:9)

9. S N R B R I D B A N Q R A T R M L (SEQ ID NO:10)

10. S N R B R I D B A N Q R A T R M (SEQ ID NO:11)

11. S N R T R I D Q A N Q R A T R M (SEQ ID NO:12)

12. S N R T R I D B A N Q R A T R M (SEQ ID NO:13); and

13. S N R T R I D B A N Q R A T R M L (SEQ ID NO:14).

6. The method of claim 2 wherein, said substrate peptide is S N R B R I D Q A N Q R A B R X L (SEQ ID NO:15).

7. The method of claim 2 wherein, said substrate peptide contains modified lysine residues.

8. The method of claim 2 wherein, said label is fluorescamine.

9. A method for screening compounds suspected of inhibiting or activating botulinum neurotoxin type A, said method comprising:

(i) combining said compound with botulinum neurotoxin type A and a substrate peptide for said botulinum according to claim 1 such that hydrolysis of said peptide is initiated;

(ii) measuring amount of hydrolysis by combining a detectable label able to detect free amino groups resulting from said hydrolysis; and (iii) detecting an inhibition or activation of botulinum neurotoxin type A by detecting a decrease or increase, respectively, in hydrolysis compared to a similar measurement produced from a reaction without the presence of said compound.

10. A kit for measuring botulinum neurotoxin type A in a sample said kit containing in close confinement (i) a container containing a known amount of botulinum neurotoxin type A;

(ii) a container containing said peptide substrate of botulinum neurotoxin type A as claimed in claim 1;

(iii) a container containing a label able to detect free amino groups resulting from the hydrolysis of said peptide; and (iv) a container or containers containing cofactors and buffers necessary for conducting said assay.

11. The substrate peptide according to claim 1 wherein said peptide is chosen from the group consisting of:

1. S N R T R I D E A N Q R A T R N L (SEQ ID NO:2)

2. S N R T R I D Q A N Q R A T R M L (SEQ ID NO:3)

3. S N R B R I D E A N Q R A T R M L (SEQ ID NO:4)

4. S N R T R I D E A N Q R A B R M L (SEQ ID NO:5)

5. S N R T R I D E A N Q R A T R X L (SEQ. ID NO:6)

6. S N R B R I D E A N Q R A T R M (SEQ ID NO:7)

7. S N R B R I D Q A N Q R A T R M L (SEQ ID NO:8)

8. S N R B R I D Q A N Q R A T R M (SEQ ID NO:9)

9. S N R B R I D B A N Q R A T R M L (SEQ ID NO:10)

10. S N R B R I D B A N Q R A T R M (SEQ ID NO:11)

11. S N R T R I D Q A N Q R A T R M (SEQ ID NO:12)

-continued

12. S N R T R I D B A N Q R A T R M (SEQ ID NO:13)

13. S N R T R I D B A N Q R A T R M L (SEQ ID NO:14)

14. S N R T R I D E A N Q R A T R M (SEQ ID NO:51)

15. S N R T R I D E A N Q R A T R X (SEQ ID NO:52)

16. S N R B R I D E A N Q R A T R X (SEQ ID NO:53)

17. S N R T R I D Q A N Q R A T R X (SEQ ID NO:54)

18. S N R T R I D B A N Q R A T R X (SEQ ID NO:55);

-continued and

19. S N R R R I D B A N Q R A T R X (SEQ ID NO:56).

12. The substrate peptide according to claim 1 wherein said peptide is S N R B R I D Q A N Q R A B R X L (SEQ ID NO:15).

13. A substrate peptide according to claim 1 wherein lysines at positions 3 and 15 of said peptide are substituted with arginine.

* * * * *